United States Patent
Radicke et al.

(10) Patent No.: US 11,013,478 B2
(45) Date of Patent: May 25, 2021

(54) APPARATUS AND METHOD FOR A MAMMOGRAPHY SYSTEM

(71) Applicant: Siemens Healthcare GmbH, Erlangen (DE)

(72) Inventors: Marcus Radicke, Veitsbronn (DE); Thomas Mertelmeier, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/540,308

(22) Filed: Aug. 14, 2019

(65) Prior Publication Data
US 2020/0060633 A1  Feb. 27, 2020

(30) Foreign Application Priority Data
Aug. 22, 2018 (EP) .................................. 18190255

(51) Int. Cl.
| | |
|---|---|
| *A61B 6/04* | (2006.01) |
| *A61B 6/00* | (2006.01) |
| *A61B 8/08* | (2006.01) |
| *A61B 8/00* | (2006.01) |
| *A61B 6/03* | (2006.01) |

(52) U.S. Cl.
CPC .......... *A61B 6/0414* (2013.01); *A61B 6/4417* (2013.01); *A61B 6/502* (2013.01); *A61B 8/0825* (2013.01); *A61B 8/403* (2013.01); *A61B 6/032* (2013.01); *A61B 8/4281* (2013.01)

(58) Field of Classification Search
CPC ... A61B 6/0414; A61B 6/4417; A61B 8/0825; A61B 8/403; A61B 6/502; A61B 8/4281; A61B 6/032
See application file for complete search history.

(56) References Cited

U.S. PATENT DOCUMENTS

| | | | |
|---|---|---|---|
| 2005/0207528 A1 | 9/2005 | Hjarn | |
| 2007/0249925 A1* | 10/2007 | Hoheisel | A61B 5/0537 600/407 |
| 2013/0129039 A1 | 5/2013 | DeFreitas et al. | |
| 2014/0328458 A1* | 11/2014 | Erhard | A61B 6/548 378/37 |

(Continued)

FOREIGN PATENT DOCUMENTS

| | | |
|---|---|---|
| DE | 102012212135 A1 | 1/2014 |
| DE | 102015218607 A1 | 3/2017 |
| EP | 3372168 A1 | 9/2018 |

OTHER PUBLICATIONS

European Search Report for European Patent Application No. 18190255 dated Feb. 7, 2019.

*Primary Examiner* — Kiho Kim (74) *Attorney, Agent, or Firm* — Harness, Dickey & Pierce, P.L.C.

(57) ABSTRACT

In an apparatus and associated method, by analyzing video images of compression of a breast of a patient in a compression unit, an actual contact-area of the tissue of the breast of the patient, which tissue is pushed onto a gauze of a compression element of the compression unit, is increased by changing a volume. As such, a pressure is increased, in at least one sub-chamber of a positioning unit integrated in the compression unit, such that the actual contact-area matches a first area, which is the maximum possible based on an outer contour of the breast.

17 Claims, 4 Drawing Sheets

(56) References Cited

U.S. PATENT DOCUMENTS

| | | | |
|---|---|---|---|
| 2015/0036796 A1* | 2/2015 | Dornberger | A61B 6/54 378/37 |
| 2015/0351706 A1 | 12/2015 | Nanke et al. | |
| 2019/0090828 A1 | 3/2019 | Dederichs et al. | |
| 2020/0146652 A1* | 5/2020 | Arai et al. | A61B 6/0414 |

* cited by examiner

APPARATUS AND METHOD FOR A MAMMOGRAPHY SYSTEM

PRIORITY STATEMENT

The present application hereby claims priority under 35 U.S.C. § 119 to European patent application number EP 18190255.2 filed Aug. 22, 2018, the entire contents of each of which are hereby incorporated herein by reference.

FIELD

Embodiments of the invention generally relate to invention relates to an embodiment and to an associated method for a mammography system.

BACKGROUND

Different imaging techniques for creating diagnostic images of a body region of a patient are often needed in order to localize and verify pathological symptoms. For an initial diagnosis, it would be possible, for example, to produce ultrasound acquisitions and individual or 3D X-ray acquisitions and to reproduce the acquisitions on screens independently of one another. A potential attribution of abnormalities in the X-ray or ultrasound image lies within the judgment of the doctor providing treatment.

In order to provide a verified diagnosis, for example after a breast examination, ultrasound acquisitions in addition to mammography and/or X-ray tomosynthesis acquisitions are created from the breast of a patient during one session. Specific preparations and/or presets are needed for each type of acquisition.

The X-ray images produced by the X-ray technology and the ultrasound images produced by the ultrasound technology can both be produced during a breast examination and can be reproduced individually or jointly and/or in superposition on a screen for the purpose of assessment. There is broad agreement among experts that currently it is only possible by the skillful combination of different imaging techniques to obtain a diagnosis that has both high sensitivity and specificity.

Superimposing different types of acquisition requires the breast to be immobilized, or more specifically compressed, for instance between two compression surfaces, so that these acquisitions can be created immediately in succession, and the 2D or 3D X-ray image and the ultrasound view can be spatially registered with one another. The resultant acquisitions from the X-ray and ultrasound examination can each produce both two-dimensional and three-dimensional views, which are then combined in a known manner or are presented such that they have at least a spatial correspondence, in order to provide a doctor with a tool for rapid and informative diagnosis.

Whereas with mammography and/or X-ray images for a tomosynthesis acquisition it is necessary, inter alia, to make a patient-specific adjustment such as the X-ray dose, when creating an ultrasound acquisition it must be ensured that the ultrasound waves are transmitted directly into and out of the breast tissue. Keeping within these constraints, especially for creating an ultrasound acquisition, places high demands on the individual apparatus when the X-ray acquisition(s) and the ultrasound acquisition are to be created while maintaining the breast compression and breast geometry. In order to ensure consistency of the acquisition geometry or acquisition situation under which both the X-ray and the ultrasound examination are created, the transducer used for the ultrasound scan is integrated in the compression unit of an X-ray mammography system. Existing embodiments of ultrasound apparatuses have the disadvantage, however, that it is very difficult for ultrasound waves to reach peripheral regions of the breast tissue.

In order to reduce transition resistances for ultrasound waves, it is standard practice to apply a liquid gel between the ultrasound transducer and the surface of the breast of the patient and to remove this gel again after the ultrasound acquisition, without maintaining the breast compression. This procedure, however, has the disadvantage that it is not possible to register an X-ray acquisition with an ultrasound acquisition.

Laid-open application DE 102012212135 A1, for example, discloses an apparatus for an X-ray acquisition and ultrasound scan of a breast. This document depicts and describes a mammography system that has a compression system formed by top and bottom compression elements and comprises both an X-ray system and an ultrasound system. For the ultrasound scan, an ultrasound transducer mounted on a displacement element mechanism is moved over the top compression element in order to acquire image information then located perpendicularly beneath the transducer, in order to combine the information with the corresponding X-ray image information. This embodiment, however, has the disadvantage for an ultrasound scan that the image information to be captured in the peripheral region can degrade as a result of higher transition resistances.

As already mentioned above, a coupling gel is used in order to improve the passage of the ultrasound waves from the ultrasound transducer of the ultrasound unit into the tissue of the breast of the patient. The coupling gel provides a lower transition resistance for the ultrasound waves that the ultrasound transducer emits and re-receives. This coupling gel is applied, for example, to the gauze of the top compression element, and diffuses, for example, through the gauze into the transition regions, in which the breast surface departs from the underside of the top compression element and extends to the bottom compression element. With previously known compression apparatuses, the breast is compressed and hence immobilized, so that it is possible to superimpose the ultrasound image on the X-ray image.

Patent application EP 17193206, for example, describes an improvement for capturing the transition regions. This document proposes an apparatus and a method having at least one air cushion, which pushes in particular transition regions of the breast of the patient onto the underside of a top compression apparatus covered by a gauze, in order to facilitate thereby improved coupling of the ultrasound waves. In this apparatus, the air pressure in the air cushion(s) is raised in a typical manner. Despite the improved coupling, the ultrasound imaging is able to capture partial peripheral regions only to a limited extent.

SUMMARY

Embodiments of the invention are directed to an apparatus and a method for ultrasound image acquisition such that even the peripheral regions of a breast of a patient can be captured by an ultrasound image like in an X-ray image.

At least one embodiment is directed to an apparatus including a compression unit for compressing a breast of a patient, which compression unit is formed by at least one compression element and by a positioning unit comprising at least one sub-chamber, wherein in the compression unit, a recording unit monitors in a patient-specific manner the pressure on the breast of the patient that is to be compressed.

In the first pressure control unit are integrated a first segmentation/area-defining unit and a second segmentation/area-defining unit for defining a first area and second area. The first area is defined by an outer contour of the breast of the patient and the edge of the compression element that faces the patient, and a second area is defined by an actual contact-line and the edge of the compression element that faces the patient. A second pressure control unit, which is integrated in the first pressure control unit, changes the pressure in at least one air cushion of the positioning unit such that the breast of the patient that is embedded therein is pushed against at least one compression element of the compression unit, wherein in at least a first region, the pressure on the breast immobilized in the compression unit can be changed such that the dimensions of the second area converge with the dimensions of the first area in at least this first region.

At least one embodiment is directed to an apparatus, comprising:
  a compression unit to compress a breast of a patient, the compression unit including at least one compression element and a positioning unit including at least one sub-chamber; and
  a first pressure control unit to monitor compression of the breast of the patient using at least one sensor, and to control the compression of the breast of the patient in a patient-specific manner.

At least one embodiment is directed to a method having a compression unit for compressing a breast of a patient. The compression unit is formed by at least one compression element and by a positioning unit comprising at least one sub-chamber. The compression of the breast of the patient is controlled under sensor monitoring in a patient-specific manner.

At least one embodiment is directed to a method, for an apparatus including a compression unit to compress a breast of a patient, the compression unit including at least one compression element and a positioning unit including at least one sub-chamber, the method comprising:
  monitoring compression of the breast of the patient using at least one sensor; and
  controlling compression of the breast of the patient via the compression unit, based upon the monitoring, in a patient-specific manner.

BRIEF DESCRIPTION OF THE DRAWINGS

An exemplary embodiment of the invention is described in greater detail below with reference to drawings, without however being restricted thereto, and in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

By the apparatus provided in at least one embodiment and the associated method of at least one embodiment, a first pressure control unit is provided in a compression unit for compressing a breast of a patient, which compression unit is formed by at least one compression element and by a positioning unit comprising at least one sub-chamber, wherein in the compression unit, a recording unit monitors in a patient-specific manner the pressure on the breast of the patient that is to be compressed. In the first pressure control unit are integrated a first segmentation/area-defining unit and a second segmentation/area-defining unit for defining a first area and second area. The first area is defined by an outer contour of the breast of the patient and the edge of the compression element that faces the patient, and a second area is defined by an actual contact-line and the edge of the compression element that faces the patient. A second pressure control unit, which is integrated in the first pressure control unit, changes the pressure in at least one air cushion of the positioning unit such that the breast of the patient that is embedded therein is pushed against at least one compression element of the compression unit, wherein in at least a first region, the pressure on the breast immobilized in the compression unit can be changed such that the dimensions of the second area converge with the dimensions of the first area in at least this first region.

At least one embodiment of the invention has an advantage wherein the capture of the peripheral regions by the ultrasound imaging is equal to that extent of the breast of the patient that can be captured by the X-ray imaging.

At least one embodiment of the invention has an advantage that at least one compression plate, the impression area of a breast to be compressed is monitored, and the contact pressure for the breast of the patient can be controlled in a patient-specific manner from the monitoring data.

At least one embodiment of the invention has an advantage that pressing the breast of the patient at least onto the top compression element of the compression apparatus is monitored visually.

At least one embodiment of the invention has an advantage that a controllable pressure is increased in a patient-specific manner in the positioning unit, which is formed, for example, from a plurality of sub-chambers, the volume of at least one sub-chamber is increased, and thereby at least one peripheral region of the breast is pushed more completely onto the top compression element and this region can also be captured by the ultrasound acquisition.

At least one embodiment of the invention has an advantage that during a breast examination, the X-ray acquisition and ultrasound acquisition can be created in an immobilization phase of the breast in a compression unit, and hence the advantages of the X-ray acquisition and the ultrasound acquisition can be depicted in a view on a screen and can be used by the doctor or the doctor's assistants for diagnosis.

At least one embodiment of the invention has an advantage that a controllable pressure can be established in the chamber or the sub-chambers of the positioning unit in a patient-specific manner.

At least one embodiment of the invention has an advantage that the pressure that can be exerted on the tissue of the breast of a patient can be controlled partially and in a patient-specific manner.

At least one embodiment of the invention has an advantage that the data required for the pressure control in a chamber or the sub-chambers of the positioning unit can be derived or determined by way of visual monitoring of the contact area of the tissue of the breast against a compression element.

At least one embodiment of the invention has an advantage that the data required for the pressure adjustment can be determined by sensors integrated in and/or on or against the compression plates.

The subject matter of each of the further claims contains advantageous embodiments of the apparatus according to the invention and of the associated method.

In an apparatus and the associated method of at least one embodiment, by analyzing video acquisitions of compression of a breast of a patient in a compression unit, an actual contact-area of the tissue of the breast of the patient, which tissue is pushed onto a gauze of a compression element, is obtained by changing a volume, and hence a pressure, in at least one sub-chamber of a positioning unit integrated in the compression unit such that the actual contact-area matches a first area, which is the maximum possible based on the outer contour of the breast.

Figure 1:
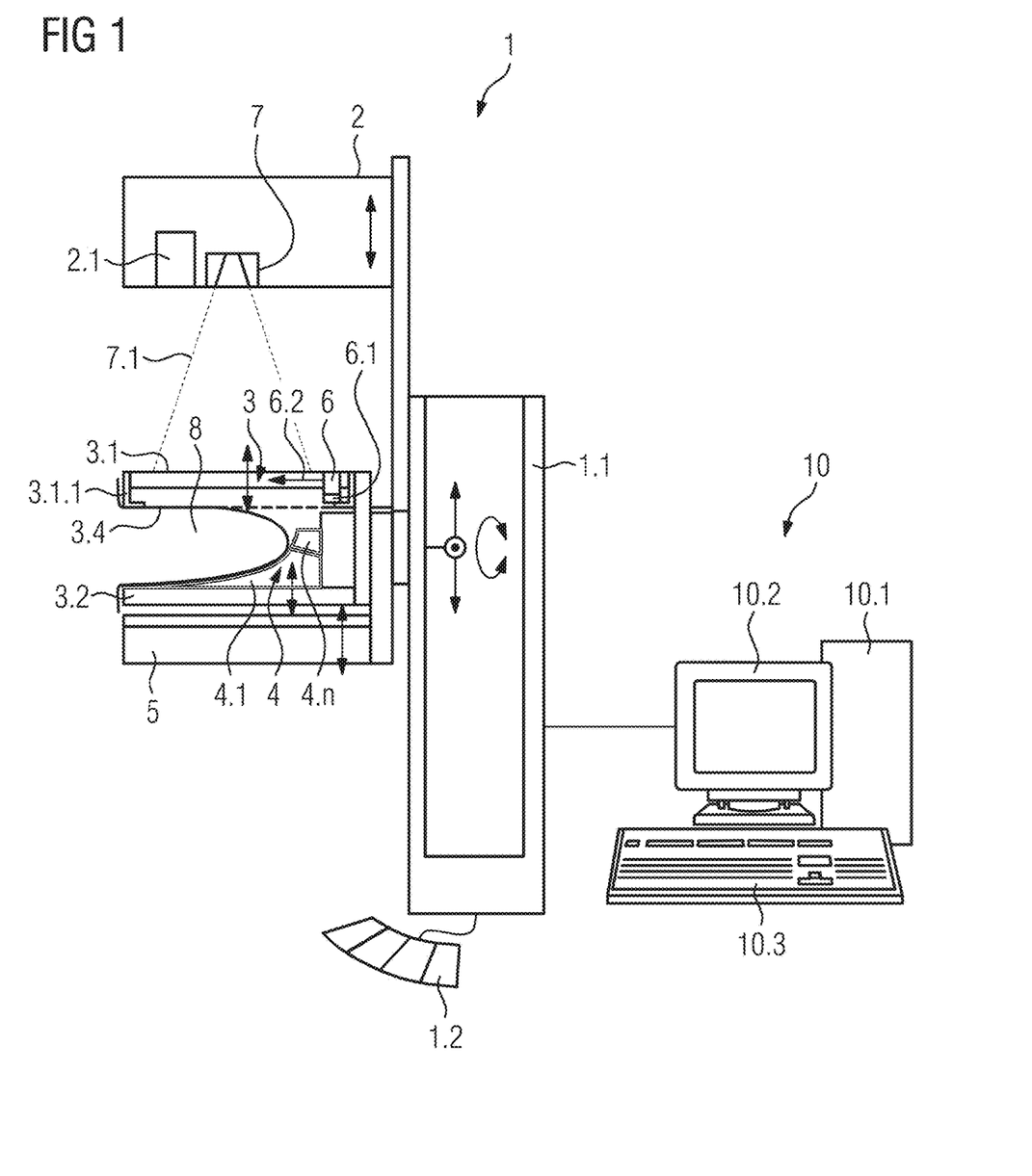
FIG. 1 shows a mammography system.

FIG. 1 shows schematically a mammography system 1. In this mammography system 1 are arranged an X-ray unit formed from X-ray source 2.1 and a detector 5, and an ultrasound unit 6 integrated in a compression unit 3 formed from top and bottom compression elements 3.1, 3.2. The mammography system 1 is controlled by control programs, for example which run in the stand of the mammography system 1 itself and/or in a data processing unit 10 connected to the mammography system 1.

A viewer can select and display on a visualization unit 10.2 of the data processing unit 10 individually, in combination and/or in superposition the mammography and/or tomosynthesis images processed by image processing programs in a processor unit 10.1 of the data processing unit 10, the ultrasound images or video images. The video images from a recording unit 7 integrated close to the X-ray source 2.1 can be processed in real time in the data processing unit 10. The compression unit 3 of the mammography system 1 can be controlled and/or operated, for example, via input device 10.3 at the data processing unit 10 and/or by way of function switches directly at the mammography system 1 and/or at at least one pedal switch 1.2.

For an X-ray and/or ultrasound acquisition, the breast of a patient 8 is immobilized in the compression unit 3, for example. The tissue of the breast of the patient 8 is immobilized and/or compressed here, for example, between a frame 3.1.1 of a top compression element 3.1, which frame is covered by a gauze 3.4, and a bottom compression element 3.2. The surface of a detector 5 can also be used as the bottom compression element 3.2. The frame 3.1.1 of the top compression element 3.1, which frame is covered by the gauze 3.4, can also be designated the top compression plate.

A coupling gel, for example, is applied to the gauze 3.4 and/or to the breast tissue of the breast of the patient 8 in order to improve the supply of the ultrasound waves from the ultrasound transducer 6.1 of the ultrasound unit 6 to the tissue of the breast of the patient 8. The ultrasound unit 6 can be moved in the directions 6.2 indicated. The coupling gel is applied to the gauze 3.4 after an X-ray acquisition and before an ultrasound acquisition, and diffuses, for example partially, through this gauze onto the tissue surface of the breast of the patient 8, and hence forms a coupling medium between the ultrasound unit 6 and the breast tissue, thereby reducing the transition resistances for the ultrasound waves that the ultrasound transducer 6.1 emits and re-receives.

Between the top and bottom compression elements 3.1, 3.2 is arranged a positioning unit 4 formed from at least one sub-chamber 4.1, . . . , 4.*n*. The at least one sub-chamber 4.1, . . . , 4.*n* of the positioning unit 4 is filled with a medium in a patient-specific manner during the immobilization and/or compression phase.

In the X-ray enclosure 2 is integrated, for instance close to the X-ray head 2.1, a recording unit 7 that records the compression process. The aperture angle of the recording unit 7 is selected such that the recording or acquisition region 7.1 captures at least the rear face of the top compression element 3.1. The top compression element 3.1, since it includes a gauze 3.4 clamped in a frame 3.1.1, facilitates the detection of the breast of the patient 8 that is embedded in and/or resting on the bottom compression element 3.2 in the positioning unit 4. If the breast is being immobilized for an X-ray acquisition and/or ultrasound acquisition, then it is compressed and/or immobilized between the top and bottom compression elements 3.1, 3.2 in a first compression step. In a further step, the pressure and hence the volume in at least one sub-chamber 4.1, ..., 4.$n$ of the positioning unit 4 is changed in a patient-specific manner under visual monitoring.

Figure 2:
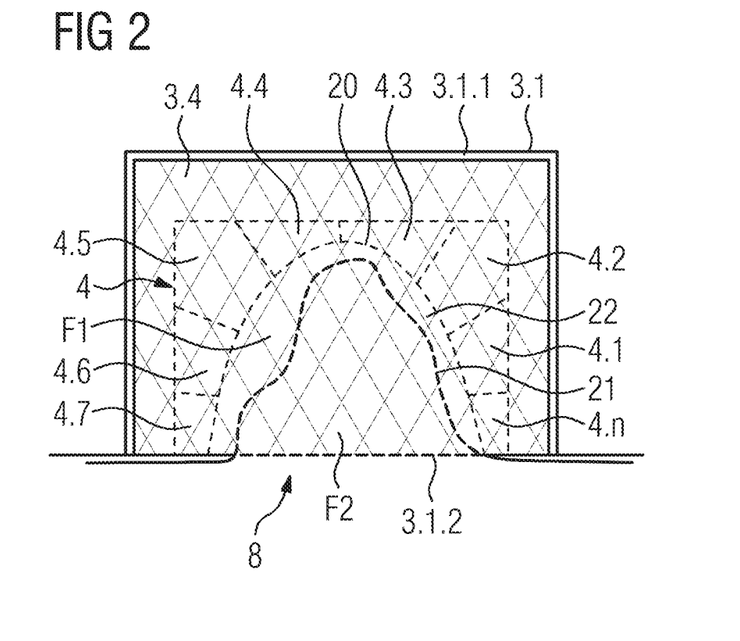
FIG. 2 is a plan view.

FIG. 2 shows the recording or acquisition region 7.1, indicated in FIG. 1, of the recording unit 7. The dimensions of the recording region 7.1 and the resolution of the recording unit 7 are adjusted such that the contour of the breast and the impression of the breast of the patient 8 in the gauze 3.4, which is clamped in the frame of the top compression element 3.1.1, are captured visually and each can be selected and/or depicted by image processing programs. In the top left corner of the frame 3.1.1 of the top compression element 3.1 is indicated the gauze 3.4 clamped therein.

The figure also shows the positioning unit 4 containing the indicated individual sub-chambers 4.1, ..., 4.$n$. The sub-chamber(s) 4.1, ..., 4.$n$, for instance filled with air, at the start of the compression phase exhibit a flexible shape having at least one definable pressure. The individual sub-chambers 4.1, ..., 4.$n$ of the positioning unit 4 conform to the given shape of the breast of the patient 8, and with a rise in pressure in the sub-chamber(s) 4.1, ..., 4.$n$ cause enlargement of the respective sub-chamber(s) and hence cause the breast tissue to rise and be pressed onto, for example, the top compression element 3.1. Apart from air, temperature-controlled water or a liquid gel can also be used as the medium for increasing the pressure.

The medium in the sub-chambers 4.1, ..., 4.$n$ can have a different pressure and hence a different volume. Instead of a multiplicity of individual sub-chambers 4.1, ..., 4.$n$, a subset or a single sub-chamber as the positioning unit 4 can be arranged on the bottom compression element 3.2.

Reducing the distance between the top and bottom compression elements 3.1, 3.2, or enlarging the positioning unit 4, results in immobilization and hence compression of the breast of the patient 8. The tissue of the breast is thereby pushed against the top compression element 3.1 and into the positioning unit 4 arranged on the bottom compression element 3.2.

In a distance determination unit AE, the current breast thickness is determined by measuring the distance between the first and second compression elements 3.1, 3.2. A further reduction in the distance pushes the breast of the patient more into the shape-forming positioning unit 4. An impression formed by pushing the breast of the patient 8 onto the gauze 3.4 in the top compression element 3.1 forms an actual contact-line 21. This actual contact-line 21 and the edge 3.1.2 of the frame of the top compression element 3.1, which edge faces the patient, enclose an actual contact-area, which is designated the second area F2.

This figure also indicates the outer contour 20 of the breast of the patient 8, which outer contour can be selected by the recording unit 7. This outer contour 20 of the breast of the patient 8 can also be described as the outermost breast region that has no direct contact with the gauze 3.4 of the top compression element 3.1. Evidently, and by way of suitable image processing programs, the outer contour 20 and the actual contact-line 21 can be reproduced in a visualization unit 10.2. The breast region 22 that has no direct contact with the gauze 3.4 of the top compression element 3.1 lies between the outer contour 20 of the breast of the patient 8 and the actual contact-line 21 of the breast on the gauze 3.4.

The intention is to minimize this region 22. A segmentation/area-determination module SFM, which comprises a first segmentation/area-defining unit ESFE and a second segmentation/area-defining unit ZSFE (see FIG. 5), is used to determine first area F1, which is enclosed by the outer contour 20 and the edge of the top compression element 3.1.2 that faces the patient, and the second area F2, which is enclosed by the actual contact-line 21 and the edge of the top compression element 3.1.2 that faces the patient. The first area F1 specifies the maximum possible breast area that can be depicted. The second area F2 can also be referred to as the actual contact-area of the breast tissue with the gauze 3.4 clamped in the frame.

The actual contact-line 21 is shown in this view as having a significant difference from the outer contour 20 of the breast of the patient 8. The view also shows the positioning unit 4 containing the individual sub-chambers 4.1, ..., 4.$n$. An embodiment variant having a positioning unit 4 comprising a single chamber is equally possible. During the compression, for instance after a minimum distance between the top and bottom compression elements 3.1, 3.2 is reached, which distance is adjusted to suit the breast of the patient 8, a volume expansion is performed in selected regions in a controlled manner, during which volume expansion the first and second areas F1, F2 are calculated continuously, and the quotient of second F2 and first F1 is determined continuously in an area-comparison module FM. The quotient value is calculated and/or presented as a function of the compression force/pressure in the sub-chamber(s) of the positioning unit 4 and of the breast thickness.

If under increasing pressure in the sub-chambers 4.1, ..., 4.$n$ of the positioning unit 4, the quotient F2/F1 remains unchanged, the area-comparison module FM stops a further rise in pressure in the sub-chambers 4.1, ..., 4.$n$ on a definable threshold value being exceeded. The immobilization and/or compression of the breast of the patient is performed via a microprocessor controller. The aforementioned increase in pressure and/or volume in the sub-chamber(s) 4.1, ..., 4.$n$ of the positioning unit 4 also takes place under microprocessor control.

While a first pressure control unit LKS analyzes video acquisitions during a reduction in distance between the top and bottom compression elements 3.1, 3.2 and stops the reduction in distance, a second pressure control unit PDE (see FIG. 5) undertakes the aforementioned patient-specific pressing of the breast of the patient 8 onto the top compression element 3.1, in which process the breast region 22 that has no direct contact with the gauze 3.4 of the top compression element 3.1 is reduced. The patient-specific change in the pressure and/or volume in the sub-chamber(s) 4.1, ..., 4.$n$ of the positioning unit 4 is performed on the basis of continuous video image analysis. The distances between outer contour 20 and actual contact-line 21 are determined by the continuous image analysis, and the second pressure control unit PDE performs convergence of the actual contact-line 21 with the outer contour 20 in a first, second and third stage.

In a further embodiment variant, the region(s) 22 of the breast of the patient 8 are determined that are still without direct contact with the gauze 3.4 of the top compression element 3.1. In the case that the positioning unit 4 includes a plurality of sub-chambers 4.1, ..., 4.$n$, the second pressure control unit PDE selects in conjunction with the first segmentation/area-defining unit ESFE and/or the second segmentation/area-defining unit ZSFE the sub-chamber 4.$x$ or the sub-chambers 4.$x$, ..., 4.$y$, in which the regions 22 of the breast of the patient 8 still have no direct contact with the gauze 3.4 of the top compression element 3.1. The increase in pressure and/or volume in the individual sub-chambers 4.$x$ is performed, for example, by monitoring the distance(s) between the outer contour 20 and the actual contact-line 21.

In regions in which the differences are the largest or a definable distance is exceeded, the sub-chamber(s) of the positioning unit 4 that lie directly underneath, and also the adjoining sub-chambers, are determined, and the pressure and/or volume in the sub-chambers concerned is increased. A compression condition for a first, second or third stage may be fulfilled depending on the distance of the top compression element from the bottom compression element 3.1, 3.2. Then, depending on the analyses of the video recordings from the recording unit 7, the second pressure control unit PDE continues with the stages(s) still missing.

Proceeding from a minimum distance between the top and bottom compression elements 3.1, 3.2, which depends on the breast of the patient 8, the patient-specific compression optimization begins with one of the stages. In the first stage A1, the pressure is increased continuously in the sub-chambers 4.1, . . . , 4.n as long as the actual contact-area F2 is less than 80% of the first area F1. In the second stage A2, the pressure rise takes place at a reduced rate and/or partially in the sub-chamber(s) as soon as the actual contact-area F2 is greater than/equal to 80% and less than 95% of the first area F1. In the third stage A3, in which the actual contact-area F2 occupies greater than/equal to 95% to 100% of the first area F1, a further rise in pressure in the sub-chamber(s) takes place very slowly.

The second pressure control unit PDE prevents a further pressure rise if all the breast regions are already in contact with the gauze 3.4 of the top compression element 3.1. Suitable signaling is given to the operator of the mammography system 1 on the visualization unit 10.2 of the data processing system 10. If the distance between the outer contour of the breast of the patient 20 and the actual contact-line 21 satisfies the criteria, for instance a definable minimum, then the pressure rise in the selected sub-chambers of the positioning unit 4 is stopped.

Mechanical or electronic safety precautions are activated by activating control buttons and/or by operating the pedal switch 1.2.

Figure 3:
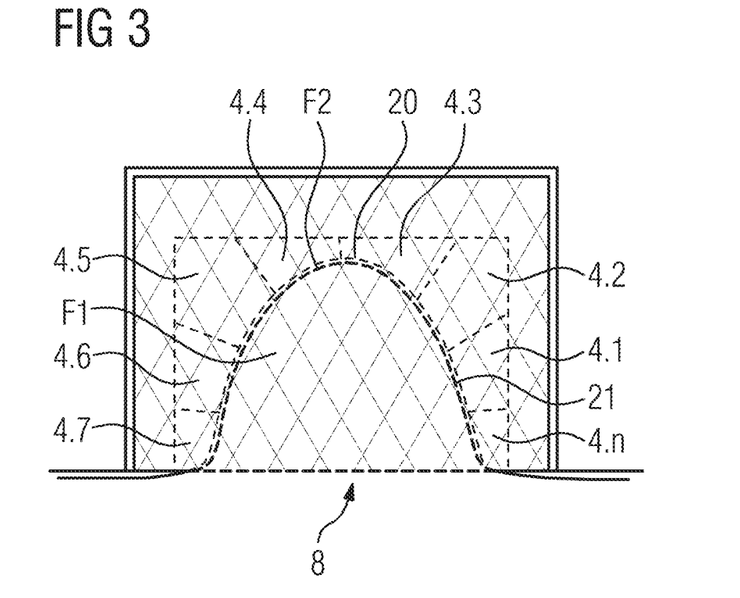
FIG. 3 is another plan view.

In FIG. 3, the maximum achievable size of the second area F2 has been achieved. The size of the second area F2 equals the size of the first area F1. The potential equality in area, or convergence, of the second area F2 with the size of the first area F1 is achieved and terminated under the control of a first/second pressure control unit LKS, PDE. The actual contact-line 21 of the breast of the patient 8 ideally matches the outer contour 20 of the breast of the patient 8.

Figure 4:
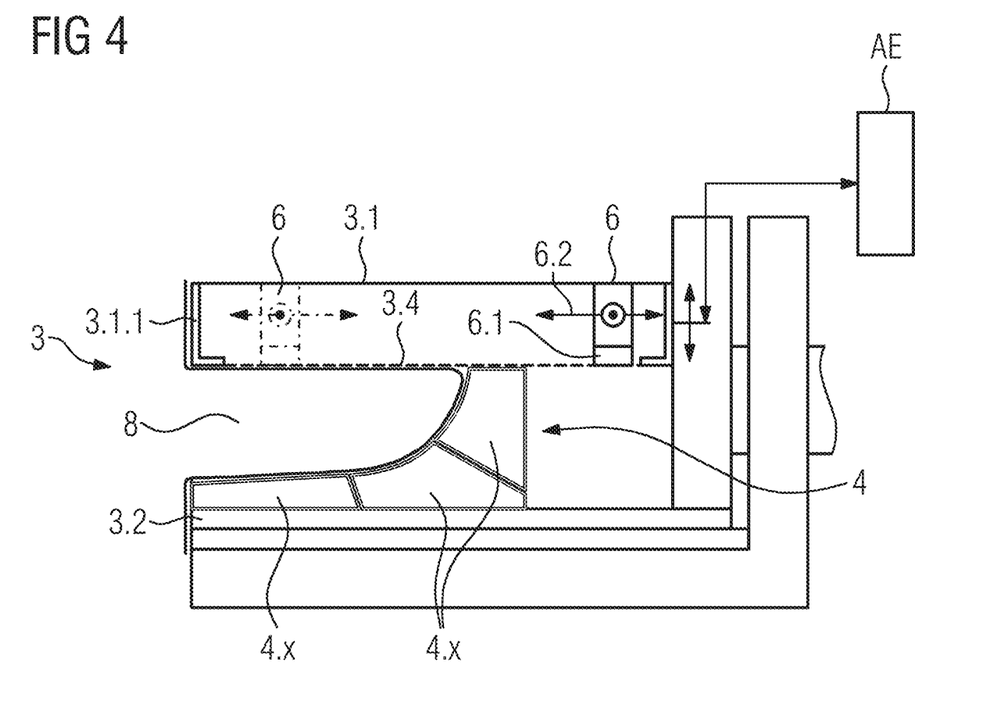
FIG. 4 is a side view.

FIG. 4 shows a side view of the compression unit 3, which contains a positioning unit 4 comprising a plurality of sub-chambers 4.x and contains an ultrasound unit 6. The shape of the embedding of the breast of the patient 8 by the positioning unit 4 can extend in a convex manner, or in segments in a convex and/or linear manner.

Figure 5:
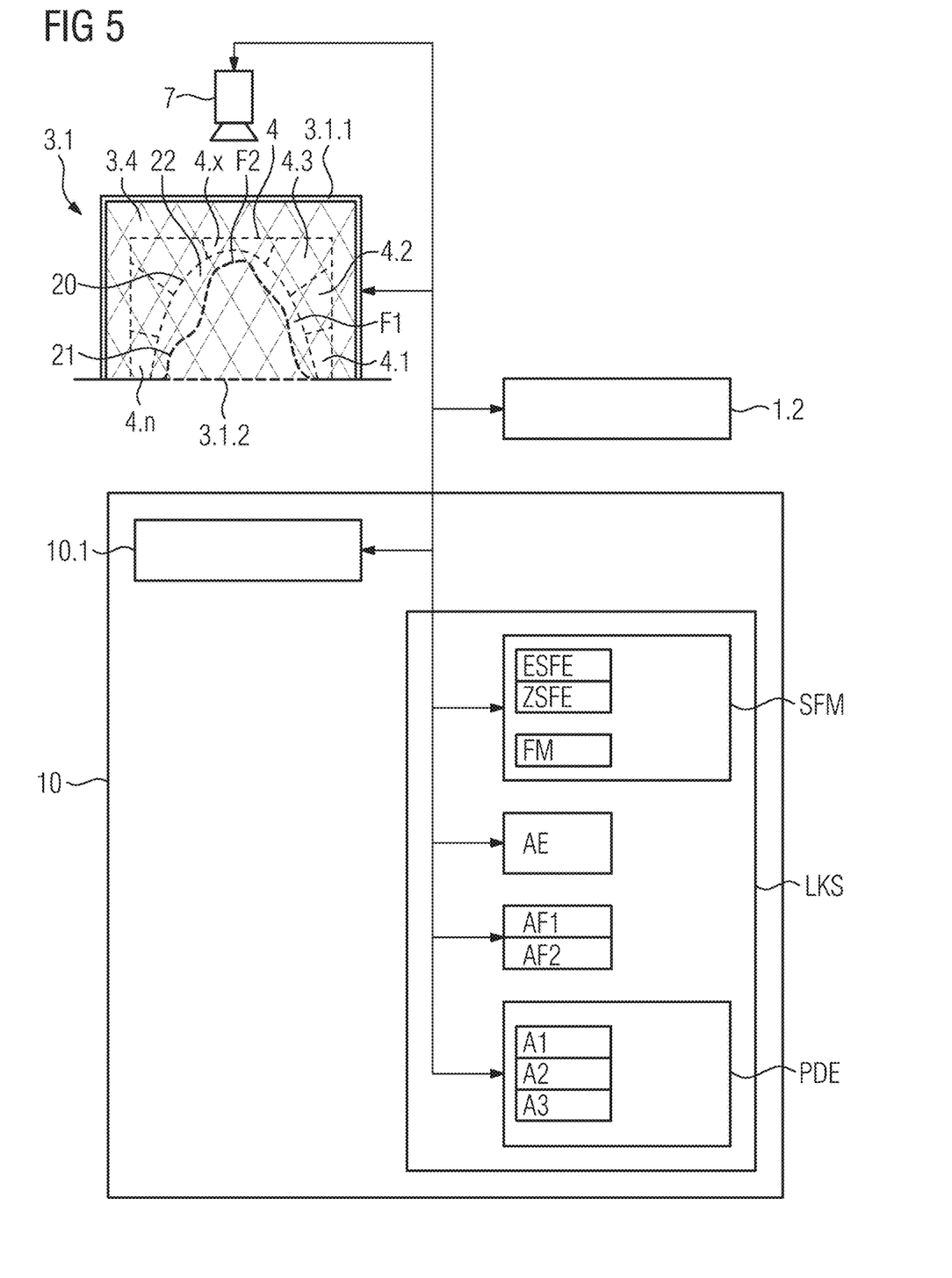
FIG. 5 is a block diagram.

FIG. 5 shows schematically a control unit and additional control units, or control modules, for patient-dependent breast compression, and the top compression element 3.1 of the compression unit 3, which compression element is captured by a recording unit 7. Sub-control-units such as segmentation/area-determination module SFM and a second pressure control unit PDE are assigned schematically as a control unit to a first pressure control unit LKS. The first and second pressure control units LKS, PDE perform patient-specific compression of the breast of the patient 8.

The compression process for compressing the breast is continued until the tissue of the breast of the patient 8 adjoins at least one compression element 3.1, 3.2 over a large area (see FIG. 3). The compression process can be terminated at any time. The acquisition unit 7 is oriented such that the recording or acquisition region 7.1 reproduces at least the rear face of the gauze 3.4 clamped in a frame 3.1.1 of the top compression element 3.1. The gauze 3.4 used is semi-transparent, for example, and allows, inter alia, the visual capture of the positioning element 4 arranged between the top and bottom compression elements 3.1, 3.2, and of the breast of the patient 8 embedded therein, and of the outline or outer contour 21 thereof and the impression thereof on the gauze 3.4.

Reducing the distance between the top and bottom compression elements 3.1, 3.2 both immobilizes and compresses the breast of the patient 8. In the process, the tissue of the breast of the patient 8 is pushed against the top compression element 3.1 and into the positioning unit 4 lying on the bottom compression element 3.2.

The tissue of the breast of the patient 8 that is pushed onto the gauze 3.4 is shown in bold cross-hatching in FIG. 5. The area of the impression is designated the second area F2. The second area F2 extends between the limit formed by the actual contact-line 21 and the edge 3.1.2 of the top compression element 3.1 that faces the patient. The positioning unit 4 and the individual sub-chambers 4.1, . . . , 4.n, if present, can also be captured by the recording unit 7.

The individual sub-chambers 4.1, . . . , 4.n of the positioning unit 4 are pre-shaped in this view or conform to the given shape of the breast of the patient 8, and with a rise in pressure produce an increase in volume of the respective sub-chambers and hence lift up the breast tissue. The volume and/or pressure can be changed, for example, by feeding air into the sub-chambers 4.1, . . . , 4.n, or a fluid such as water or a low-viscosity gel. Instead of a multiplicity of individual sub-chambers 4.1, . . . , 4.n, a subset or a single or single-piece positioning unit 4 can be arranged on the bottom compression element 3.2, as already mentioned.

The recording unit 7 captures the outer contour 20, the actual contact-line 21 and the edge 3.1.2 of the top compression element 3.1 that faces the patient, and also transfers the image data to the segmentation/area-determination module SFM, and analyzes the image data. The first segmentation/area-defining unit ESFE segments the outer contour 20 and the edge 3.1.2 of the top compression element 3.1 that faces the patient, and determines from the current outer contour 20 a maximum possible flatness, designated first area F1, of the currently-to-be-compressed breast of the patient 8. The second segmentation/area-defining unit ZSFE segments the actual contact-line 21 and the edge 3.1.2 of the top compression element 3.1 that faces the patient, and calculates continuously the second area F2, which is enclosed by the edge 3.1.2 of the top compression element 3.1 that faces the patient and by the actual contact-line 21.

In the video image from the recording unit 7 reproduced on the visualization unit 10.2 of the data processing unit 10, the outer contour 20 and the edge 3.1.2 that faces the patient are highlighted by a broken line, the actual contact-line 21 by a continuous line. The first area F1 represents the maximum possible breast area, and the second area F2 represents the area of the impression of the breast top face on the gauze 3.4 clamped in the frame 3.1.1 of the top compression element 3.1. During the compression of the breast of the patient 8, the first and second areas F1, F2 are calculated continuously by the respective segmentation/area-defining units ESFE; ZSFE, and the quotient of the second area F2 and the first area F1 is calculated continuously in an area-comparison module FM.

The calculation of the quotient of the second area and the first area F2/F1 takes into account the compression force or pressure in the positioning unit 4, in other words in the sub-chamber(s) 4.1, ..., 4.n of the positioning unit 4, and the determined current breast thickness. The compression force could be detected, for example, also by pressure sensors integrated in the compression unit 3.

In a distance determination unit AE, the breast thickness that currently exists is determined by measuring the distance between the top and bottom compression elements 3.1, 3.2. If there is no increase in the second area F2 when the distance between the top and bottom contact elements 3.1, 3.2 is reduced further, the area-comparison module FM stops a further rise in pressure, resulting from a reduction in distance, on the tissue of the breast of the patient 8 on a definable threshold value being exceeded. Stopping the pressure rise is achieved by a first switch-off unit AF1. As already suggested or mentioned also with regard to FIG. 2, the second pressure control unit PDE, which is integrated in the first pressure control unit LKS, performs closed-loop monitoring and control of the patient-specific compression of the breast.

By way of continuous analysis of image, sensor and/or pressure or measurement data, for instance in the segmentation/area-determination module SFM and in the area-comparison module FM, the first pressure control unit LKS implements in the sub-chambers 4.1, ..., 4.n of the positioning unit 4 a pressure rise in a controlled manner by reducing the distance between the top and bottom compression elements 3.1, 3.2. In this process, a convergence in terms of area of the second area F2 with the first area F1 is achieved. A further convergence between the second and first areas F1, F2 in terms of area is achieved by the control modules assigned to the second pressure control unit PDE.

The second pressure control unit PDE can also be referred to as a partial pressure control unit. The adjustment or optimization process performed by the second pressure control unit PDE is divided below into a first, second and third stage A1, A2 and A3. The embodiment of a first, second and third stage is by way of example. In the first stage A1, as already mentioned, the pressure is increased continuously in the sub-chambers 4.1, ..., 4.n, for instance by reducing the distance between the top and bottom compression elements 3.1, 3.2 or increasing the volume of the sub-chambers 4.1, ..., 4.n, as long as the actual contact-area F2 is less than 80% of the first area F1. In the second stage A2, the pressure rise takes place at a reduced rate and/or partially in the sub-chambers or a sub-chamber as soon as the actual contact-area F2 is greater than/equal to 80% and less than 95% of the first area F1.

In the third stage A3, the pressure rise, for instance by a partial volume expansion in the sub-chamber(s) 4.1, ..., 4.n of the positioning unit 4, takes place very slowly until the actual contact-area F2 occupies greater than/equal to 95% to 100% of the first area F1, in which process the volume in at least one air cushion (4.1, ..., 4.n) of the positioning unit (4) is changed such that the breast of the patient (8) that is embedded therein is pushed onto the at least one compression element (3.1, 3.2) of the compression unit (3), wherein in at least a first region, the pressure onto the breast immobilized in the compression unit (3) can be changed such that the dimensions of the second area (F2) converge with the dimensions of the first area (F1) in at least this first region. The breast of the patient adjoins over a large area when the second area F2 matches the first area F1 (see FIG. 3).

The second pressure control unit PDE changes the volume in at least one air cushion 4.1, ..., 4.n of the positioning unit 4 such that the breast of the patient 8 that is embedded therein is pushed onto the at least one compression element 3.1, 3.2 of the compression unit 3, wherein in at least a selected region, the pressure onto the breast immobilized in the compression unit 3 can be changed such that the dimensions of the second area F2 equal the dimensions of the first area F1 in at least this selected region. The second pressure control unit PDE prevents a further pressure rise if alignment between the surface area of the second and first areas F2, F1 exists or is achieved. Switching off the volume expansion in the sub-chambers is then achieved by a second switch-off unit AF2. Suitable signaling is given to the operator of the mammography system 1.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1. mammography system
1.1 stand
1.2 pedal switch
2 X-ray enclosure
2.1 X-ray head
3 compression unit
3.1 top compression element
3.1.1 frame of the top compression element
3.1.2 edge of the top compression element that faces the patient
3.2 bottom compression element
3.4 gauze
4 positioning unit
4.1., ..., 4.n sub-chambers of the positioning unit
5 detector
6 ultrasound unit
6.1 ultrasound transducer
6.2 directions of movement of the ultrasound unit 7 recording unit
7.1 acquisition region of the recording unit
8 breast of a patient
10 data processing unit
10.1 processor unit(s)
10.2 visualization unit
20 outer contour of the breast of the patient
21 actual contact-line
22 breast region that has no direct contact with the gauze of the top compression element
LKS first pressure control unit
PDE second pressure control unit
F1 first area
F2 second area
SFM segmentation/area-determination module
ESFE first segmentation/area-defining unit
ZSFE second segmentation/area-defining unit
FM area-ratio determination module
AE distance determination unit
AF1 first switch-off unit
A1 first stage
A2 second stage
A3 third stage
AF2 second switch-off unit

What is claimed is:

1. An apparatus, comprising:
a compression unit to compress a breast of a patient, the compression unit including at least one compression element and a positioning unit; and
a first pressure control unit to monitor compression of the breast of the patient, using at least one sensor, and to control the compression of the breast of the patient in a patient-specific manner, the first pressure control unit including a segmentation/area-determination module including
a first segmentation/area-defining unit to define a first area, bounded by an outer contour of the breast of the patient and an edge of a top compression element facing the patient, and
a second segmentation/area-defining unit to define a second area, bounded by a contact-line of the breast of the patient and the edge of a top compression element facing the patient.

2. The apparatus of claim 1, wherein the at least one sensor is a recording unit, wherein the breast of the patient to be compressed is monitored by the recording unit during a compression process for tissue of the breast of the patient adjoining over a large area at least one compression element of the compression unit.

3. The apparatus of claim 2, wherein the compression unit includes at least one compression element formed by a frame covered by a transparent coverings such that an outer contour of the breast of the patient, and the contact-line of the breast of the patient that is to be compressed, are visually capturable by the recording unit, the contact-line forming on the transparent covering.

4. The apparatus of claim 1, wherein the at least one sensor is a recording unit and wherein the compression unit includes at least one compression element formed by a frame covered by a transparent covering such that an outer contour of the breast of the patient, and the contact-line of the breast of the patient that is to be compressed, are visually capturable by the recording unit, the contact-line forming on the transparent covering.

5. The apparatus of claim 1, wherein the at least one sensor is a recording unit and wherein the first segmentation/area-defining unit is configured to define first area segments in the recordings from the recording unit, the outer contour of the breast of the patient, and the edge of the top compression element facing the patient, and is configured to determine the first area, bounded by the outer contour and the edge of the top compression element facing the patient, and
the second segmentation/area-defining unit is configured to define second area segments, the contact-line and the edge of the top compression element facing the patient, and is configured to determine the second area, bounded by the contact-line and the edge of the top compression element.

6. The apparatus of claim 5, wherein the first pressure control unit includes a second pressure control unit, the second pressure control unit being configured to change volume in at least one air cushion of the positioning unit such that the breast of the patient, embedded in the at least one air cushion, is pushed onto the at least one compression element of the compression unit, wherein in at least one selected region, pressure on the breast immobilized in the compression unit is changable such that dimensions of the second area match dimensions of the first area in the at least one selected region.

7. The apparatus of claim 1, wherein an ultrasound unit is integrated at least in a compression element of the compression unit.

8. The apparatus of claim 1, wherein the apparatus is integrated in a mammography system.

9. A mammography system, comprising the apparatus of claim 1, integrated in the mammography system.

10. The apparatus of claim 1, wherein the first pressure control unit includes a second pressure control unit, the second pressure control unit being configured to change volume in at least one air cushion of the positioning unit such that the breast of the patient, embedded in the at least one air cushion, is pushed onto the at least one compression element of the compression unit, wherein in at least one selected region, pressure on the breast immobilized in the compression unit is changable such that dimensions of the second area match dimensions of the first area in the at least one selected region.

11. The apparatus of claim 1,
wherein the at least one sensor is a recording unit,
wherein the first segmentation/area-defining unit is configured to define first area segments in the recordings from the recording unit, the outer contour of the breast of the patient, and the edge of the top compression element facing the patient, and is configured to determine the first area, bounded by the outer contour and the edge of the top compression element facing the patient, and
the second segmentation/area-defining unit is configured to define second area segments, the contact-line and the edge of the top compression element facing the patient, and is configured to determine the second area, bounded by the contact-line and the edge of the top compression element, and, based upon the first area and second area determined, area differences are cancelled out.

12. A method, for an apparatus including a compression unit to compress a breast of a patient, the compression unit including at least one compression element and a positioning unit, the at least one compression element including a frame covered by a transparent covering such that an outer contour of the breast of the patient, and a contact-line of the breast of the patient to be compressed, are visually capturable, the method comprising:

monitoring compression of the breast of the patient using at least one sensor;

controlling compression of the breast of the patient via the compression unit, based upon the monitoring, in a patient-specific manner; and determining a plurality of areas enclosed by the outer contour of the breast of the patient and the contact-line of the breast of the patient on the transparent covering, and, based upon the plurality of areas determined, partially determining and cancelling out area differences of the plurality of areas determined.

13. The method of claim 12, wherein the monitoring includes using the at least one sensor to visually monitor the breast of the patient to be compressed, and wherein the controlling includes terminating compression of the breast of the patient, once tissue of the breast of the patient is determined to adjoin over a large area of the at least one compression element of the compression unit.

14. The method of claim 12, the method further comprising:

changing a volume in the at least one portion of the positioning unit such that the breast of the patient, embedded in the at least portion, is pushed onto the at least one compression element of the compression unit, wherein in at least one region, pressure on the breast immobilized in the compression unit is changable such that dimensions of a second area converge with the dimensions of a first area in the at least one region.

15. A method for an apparatus including a compression unit to compress a breast of a patient, the compression unit including at least one compression element and a positioning unit, the method comprising:

monitoring compression of the breast of the patient using at least one sensor;

controlling compression of the breast of the patient via the compression unit, based upon the monitoring, in a patient-specific manner; and changing a volume in at least one portion of the positioning unit such that the breast of the patient, embedded in the at least one portion, is pushed onto the at least one compression element of the compression unit, wherein in at least one region, pressure on the breast immobilized in the compression unit is changable such that dimensions of a second area converge with the dimensions of a first area in the at least one region.

16. The method of claim 15, wherein the at least one compression element is formed by a frame covered by a transparent covering such that an outer contour of the breast of the patient, and a contact-line on the transparent covering of the breast of the patient to be compressed, are visually captured, the method further comprising determining at least one area enclosed by the outer contour of the breast of the patient and the contact-line on the transparent covering of the breast of the patient.

17. The method of claim 16, wherein the determining of the at least one area includes determining a plurality of areas, and wherein the determining includes, based upon the plurality of areas determined, partially determining and cancelling out area differences.

\* \* \* \* \*